US00PP11490P

United States Patent [19]

Trees

[11] Patent Number: Plant 11,490

[45] Date of Patent: Aug. 22, 2000

[54] GERANIUM PLANT NAMED 'BFP-1352'

[75] Inventor: Scott C. Trees, Nipomo, Calif.

[73] Assignee: Ball Floraplant, a Division of Ball Horticultural Co., West Chicago, Ill.

[21] Appl. No.: 09/114,059

[22] Filed: Jul. 10, 1998

[51] Int. Cl.[7] ..... A01H 5/00

[52] U.S. Cl. ..... Plt./330

[58] Field of Search ..... Plt./332, 324, 330

[56] References Cited

U.S. PATENT DOCUMENTS

P.P. 7,087 12/1989 Hofmann ..... Plt./329

P.P. 7,271 7/1990 Guillou et al. ..... Plt./332

P.P. 10,365 4/1998 Utecht ..... Plt./332

P.P. 10,399 5/1998 Trees ..... Plt./330

*Primary Examiner*—Howard J. Locker

*Assistant Examiner*—Kent L. Bell

*Attorney, Agent, or Firm*—C. A. Whealy

[57] ABSTRACT

A new and distinct cultivar of Geranium plant named 'BFP-1352', characterized by its numerous semi-double dark red-colored flowers; initially upright then pendant growth habit; vigorous and good basal branching; and dark green leaves without a zonation pattern.

1 Drawing Sheet

BACKGROUND OF THE INVENTION

The present invention relates to a new and distinct cultivar of Geranium plant, botanically known as *Pelargonium hortorum×peltatum,* and hereinafter referred to by the cultivar name 'BFP-1352'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the *Pelargonium peltatum* cultivar 'Fisrom', disclosed in U.S. Plant Pat. No. 7,567, as the male, or pollen parent with the proprietary *Pelargonium hortorum* selection 9380E as the female, or seed parent. The cultivar 'BFP-1352', was discovered and selected by the Inventor as a flowering plant within the progeny of the stated cross in a controlled environment in Arroyo Grande, Calif., on Sep. 15, 1996. Plants of the new Geranium differ from plants of the male parent, the cultivar 'Fisrom', primarily in plant habit and petal color.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1352'. These characteristics in combination distinguish 'BFP-1352' as a new and distinct cultivar:

1. Numerous semi-double dark red-colored flowers.
2. Initially upright then pendant growth habit.
3. Vigorous and good basal branching.
4. Dark green leaves without a zonation pattern.

The new Geranium can be compared to the cultivar 'Saint Malo' (not patented). However, in side-by-side comparisons conducted by the Inventor in Arroyo Grande, Calif., plants of the new Geranium differ from plants of the cultivar 'Saint Malo' in the following characteristics:

1. Plants of the new Geranium are less pendant than plants of the cultivar 'Saint Malo'.
2. Plants of the new Geranium have shorter lateral branches and shorter internodes than plants of the cultivar 'Saint Malo'.
3. Plants of the new Geranium have larger leaves than plants of the cultivar 'Saint Malo'.
4. Leaves of plants of the new Geranium are pubescent and do not have a distinct zonation pattern whereas leaves of plants of the cultivar 'Saint Malo' are smooth and have a distinct zonation pattern.
5. Plants of the new Geranium have more flowers per umbel and more petals and petaloids per flower than plants of the cultivar 'Saint Malo'.
6. Flower color of plants of the new Geranium is darker red than flower color of plants of the cultivar 'Saint Malo'.

A detailed comparison of plants of the cultivar 'BFP-1352' and the cultivar 'Saint Malo' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a side perspective view of a typical plant of 'BFP-1352'. Flower and foliage colors in the photograph may appear different from the actual colors due to light reflectance.

DETAILED BOTANICAL DESCRIPTION

The cultivar 'BFP-1352' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Classification:

*Botanical.*—*Pelargonium hortorum*×*peltatum* cultivar 'BFP-1352'.

*Commercial.*—Interspecific hybrid.

Parentage:

*Male parent.*—*Pelargonium peltatum* cultivar 'Fisrom', disclosed in U.S. Plant Pat. No. 7.567.

*Female parent.*—Proprietary *Pelargonium hortorum* selection 9380E.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous and freely branching.

Plant description:

*General appearance.*—Initially upright then pendant growth habit. Appropriate for 10 and 12.5-cm containers. About nine weeks are required to produced a finished 10-cm container from a rooted cutting.

*Growth and branching habit.*—Vigorous and good basal branching with about three lateral branches at the base.

*Plant height, base of plant to top of leaf plane.*—About 20.8 cm.

*Plant width.*—About 15.3 cm.

*Lateral branches.*—Length: About 8.5 cm. Internode length: About 2.4 cm. Color: 137C.

*Foliage description.*—Leaves simple, generally symmetrical, abundant, opposite. Quantity of leaves per lateral branch: About seven. Length: About 7.7 cm. Width: About 9.2 cm. Shape: Reniform with rounded apex, cordate base, lobed and crenate margin. Texture: Downy, both surfaces pubescent. Color: Fully expanded foliage, upper surface: 137A, no zonation pattern. Fully expanded foliage, lower surface: 146A. Petiole: Length: About 4.5 cm. Diameter: About 2 mm. Color: 137C.

Flower description:

*Flower type and habit.*—Dark red-colored flowers. Very freely and continuously flowering. Flowers arranged in spherical umbels arising from apical leaf axils. Umbels displayed above or beyond the foliage. Usually about seven umbels per plant. Flowers semi-double and slightly cupped. Umbels persistent.

*Flowering season.*—Year-round under greenhouse conditions. In the garden, flowering is continuous from spring through summer.

*Umbels.*—Number of flowers per umbel: About 16. Diameter: About 7 cm. Height: About 6 cm.

*Flowers.*—Diameter: About 4.7 cm. Depth (height): About 1.5 cm.

*Flower buds.*—Length: About 2 cm. Diameter: About 2 cm. Shape: Ovoid, pointed.

*Petals.*—Quantity: Ten, overlapping. Usually about three petaloids per flower. Length: About 2.2 cm. Width: About 1.4 cm. Shape: Obovate with rounded apex and entire margin. Texture: Velvety. Color: Fully opened, upper surface: Between 46A and 53A with upper petals having veins of 59A. Fully opened, lower surface: 45C.

*Petaloids.*—Irregular in shape with very narrow white base; about 1.5 cm in length and about 9 mm in width. Upper surface of petaloids originating from lower portion of flower is between 46A and 53A in color; upper surface of petaloids originating from upper portion of flower is between 46A and 53A in color and are veined, 59A; lower surface of all petaloids, 45C.

*Peduncle* (*umbel stem*).—Length: About 13.7 cm. Angle: Mostly erect. Texture: Slightly pubescent. Color: 137C.

*Pedicel* (*individual flower stem*).—Length: About 1.5 cm. Texture: Pubescent. Color: 136C with streaks of 182A.

*Reproductive organs.*—Androecium: Amount of pollen: Moderate. Pollen color: 167A. Gynoecium: Ovary color: Green.

*Disease resistance: Under commercial conditions, resistance to pathogens has not been observed.*

Seed development: Seed production has not been observed.

CHART A

| CHARACTERISTIC | 'BFP-1352' | 'SAINT MALO' |
|---|---|---|
| GROWTH HABIT | Upright to pendant | Mostly pendant |
| PLANT HEIGHT | About 20.8 cm | About 22.3 cm |
| LATERAL BRANCH LENGTH | About 8.5 cm | About 14 cm |
| INTERNODE LENGTH | About 2.4 cm | About 3 cm |
| LEAF LENGTH | About 7.7 cm | About 4 cm |
| LEAF WIDTH | About 9.2 cm | About 7.5 cm |
| LEAF TEXTURE | Pubescent | Glabrous |
| LEAF COLOR, MATURE, UPPER SURFACE | 137A, no zonation pattern | 137A with zonation pattern, 139A |
| LEAF COLOR, MATURE, LOWER SURFACE | 146A | 137C |
| NUMBER OF FLOWERS PER UMBEL | About 16 | About 12 |
| PETAL & PETALOID QUANTITY PER FLOWER | About 13 | About 8 |
| PETAL COLOR, UPPER SURFACE | Between 46A and 53A; upper petal veins, 59A | 45B/53C; upper petal veins, 59A |
| PETAL COLOR, LOWER SURFACE | 45C | 45C with 59A veins |
| PEDUNCLE ANGLE | Mostly erect | Slightly outward |
| PEDUNCLE LENGTH | About 13.7 cm | About 13.2 cm |

It is claimed:

1. A new and distinct cultivar of Geranium plant named 'BFP-1352', as illustrated and described.

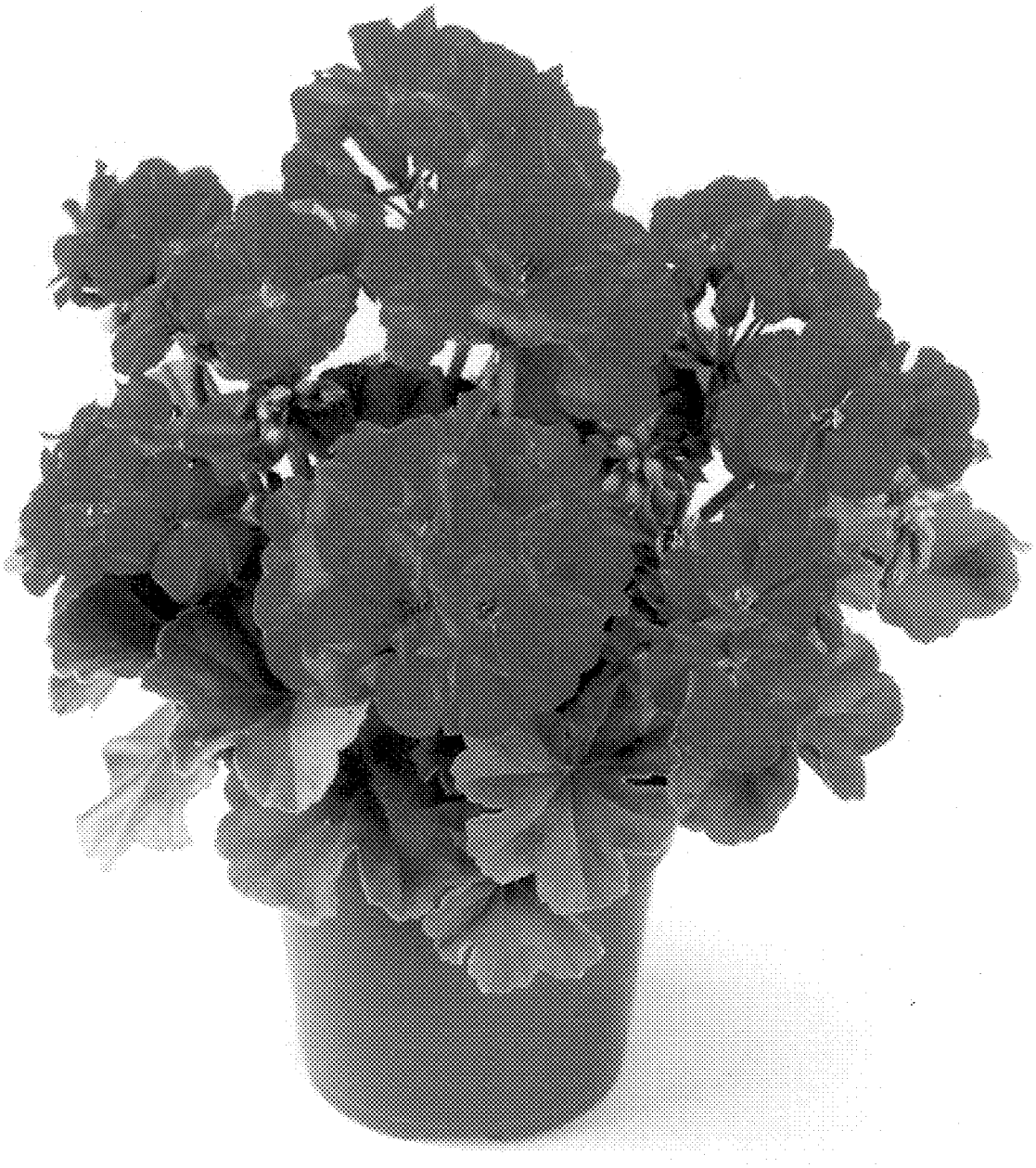

* * * * *